United States Patent [19]

Norcini et al.

[11] Patent Number: 5,716,943

[45] Date of Patent: Feb. 10, 1998

[54] PHOSPHINIC ACID DERIVATIVES WITH METALLOPEPTIDASE INHIBITORY ACTIVITY

[75] Inventors: Gabriele Norcini, Vizzola Ticino; Daniela Botta, Como; Francesco Santangelo, Milan; Claudio Semeraro, Bresso, all of Italy

[73] Assignee: Zambon Group. S.p.A., Vicenza, Italy

[21] Appl. No.: 671,149

[22] Filed: Jun. 6, 1996

[30] Foreign Application Priority Data

Jun. 14, 1995 [IT] Italy .................. MI95A1257

[51] Int. Cl.$^6$ .......... A61K 31/66; A61K 31/67; C07F 9/36
[52] U.S. Cl. .......... 514/92; 514/119; 548/117; 562/15
[58] Field of Search .......... 548/117; 514/92, 514/119; 562/15

[56] References Cited

U.S. PATENT DOCUMENTS

| | | | |
|---|---|---|---|
| 4,379,146 | 4/1983 | Greenlee et al. | 424/177 |
| 4,432,972 | 2/1984 | Karanewsky et al. | 424/177 |
| 5,151,414 | 9/1992 | Casagrande et al. | 514/114 |
| 5,451,608 | 9/1995 | Santangelo et al. | 514/674 |

FOREIGN PATENT DOCUMENTS

| | | |
|---|---|---|
| 2116559 | 10/1983 | United Kingdom . |
| 9535302 | 12/1995 | WIPO . |

OTHER PUBLICATIONS

*A Continuous Spectrophotometric Assay for Angiotensin Converting Enzyme,*Analytical Chemistry, Holmquist et al, Nov. 1978.
*Enkephalinase Activity in Rat Peripheral Organs,*Llorens et al., European Journal of Pharmacology, 1981.
*Perspectives in Medicinal Chemistry,*Testa et al., Verlag Helvetica chimica Acta, Basel, 1993.
*The Merck Index,* 11th Edition, Merck & Co., Inc., 1989.
*Synthesis and Radioiodination of N–Boc–p–(tri–n–butyl-stannyl)–L–phenylalaninee Tetrafluorophenyl Ester...,*Wilbur et al, Advance ACS Abstracts, Oct. 15, 1993.
*Inhibition of Stromelysin–1 (MMP–3) By Peptidyl Phosphinic Acids,*Goulet, J. et al, Bioorganic & Medical Chemistry Letters, vol. 4, 1994.
*A Singple Asymmetric Synthesis of 4–Arylphenylalanines via Palladium–Catalyzed Cross–Coupling Reaction of Arylboronic Acids wWith Tyrosine Triflate,*Sheih et al, Journal of Organic Chemistry, 1992.
*Phosphinic Acid Inhibitors of D–Alanyl–D–alanine Ligase,* Parsons et al., Journal of Medical Chemistry, 1988.
*On the Prediction of Binding Properties of Drug Molecules by Comparative Molecular Field Analysis,*Klebe et al, Journal of Medical Chemistry, 1993.

*Differential Binding Energy: A Detailed Evaluation of the Influence of Hydrogen–Bonding and Hydrophobic Groups on the Inhibition of Thermolysin by Phosphorus–Containing Inhibitors,*Morgan et al., American Chemical Society, 1991.
*Binding Energetics of Phosphorus–Containing INhibitors of Thermolysin,*Grobelny et al, Biochemistry 1989.
*Phosphinates as transition–state analog inhibitors of thermolysin: the importance of hydrophobic and hydrogen bonding effects,*Morgan et al, Chemical Abstracts, vol. 115, 1991.
De Lambert et al, Dual Inhibition of Neutral Endopeptidase and Angiotensin–converting enzyme by N–Phosphonnomethyl and N–Carboxyalkyl Dipeptides, Bioorg. Med. Chem. Lett. vol. 4 (22) pp.2715–2720, 1994.
Mutschler, Drug Actions, pp. 360, 361, 384, 385, 1995.
Merz et al., "Free Energy Perturbation Simulations of the Inhibition of Thermolysin: Prediction of the Free Energy of Binding of a New Inhibitor", *J. Am. Chem. Soc.*, vol. 111, No. 15 (1989), pp. 5649–5658.
Mookhtiar, K.A. et al., "Phosphonamidate Inhibitors of Human Neutrophil Collagenase". *Biochemistry*, vol. 26, No. 7 (1987), pp. 1962–1965.
McMahon et al., "Phosphoramidon Blocks the Presser Activity of Porcine Big Endothelin–1–(1–39) In Vivo and Conversion of Big Endothelin–1–(1–39), 2 Endothelin–1–(1–21) In Vitro", *Proceedings National Academy of Science,* vol. 88 (Feb. 1991), pp. 703–707.
Fukuroda, T. et al., "Inhibition of Biological Action of Big Endothelin–1 by Phosphoramidon", *Biochemical and Biophysical Research Communication,* vol. 172, No. 2 (Oct. 30, 1990), pp. 390–395.
Rich, H. David, "Peptidase Inhibitors" in *Comprehensive Medicinal Chemistry: The Rational Design, Mechanistic Study & Therapeutic Application of Chemical Compounds,* vol. 2 (Pergamon Press PLC), pp. 391–496 1990.
Kam, C.M. et al., "Inhibition of Thermolysin and Carboxy Peptidase A Biphosphoramides", *Biochemistry,* vol. 18, No. 14 (1979), pp. 3032–3038.

*Primary Examiner*—Joseph McKane
*Attorney, Agent, or Firm*—Watson Cole Stevens Davis, P.L.L.C.

[57] ABSTRACT

Compounds of formula $$R-(O)_n-CONH-CH(R_1)-P(=O)(OH)-CH_2-C(R_2)(R_3)-CONH-\overset{*}{C}H(CH_2-R_4)-COOH \quad (I)$$

wherein R, $R_1$, $R_2$, $R_3$, $R_4$ and n have the meanings reported in the description are described.

The compounds of formula I are endowed with a dual ACE-inhibitory and NEP-inhibitory activity and are useful in the treatment of cardiovascular diseases.

8 Claims, No Drawings

PHOSPHINIC ACID DERIVATIVES WITH METALLOPEPTIDASE INHIBITORY ACTIVITY

"Phosphinic acid derivatives with metallopeptidase inhibitory activity"

The present invention relates to phosphinic acid derivatives and, more particularly, it relates to phosphinic acid derivatives useful in the treatment of cardiovascular diseases as metallopeptidase inhibitors.

The pharmacologic interest towards the study of metallopeptidase inhibitory molecules derives from the role that said enzymes exert on the level of the cardiocirculatory system.

It is well-known in fact that compounds with angiotensin converting enzyme (ACE) inhibitory activity are mainly useful in the treatment of hypertension, heart failure and post-infarct since they inhibit the formation of angiotensin II, a substance which increases the blood pressure.

Compounds with endothelin convening enzyme (ECE) inhibitory activity are useful as anti-vasoconstrictors in that they inhibit the formation of endothelin, a 21 amino acid peptide with vasoconstrictor activity.

Instead, compounds with inhibitory activity of the neutral endopeptidase (NEP) enzyme, also called enkephalinase, are useful as vasodilators and diuretics in that the NEP enzyme is responsible for the inactivation, not only of endogenous enkephaline, but also of some natriuretic factors among which, for instance, the atrial natriuretic factor (ANF), a vasodilating hormone secreted by heart.

Therefore, even exerting their action on the cardiovascular system with different mechanisms of action, the compounds with metallopeptidase inhibitory activity are generally used, alone or in combination, in the treatment of hypertension, renal failure, congestive heart failure and post-infarct.

In the U.S. Pat. No. 5,476,847 (Schering Corp.) some phosphinyl-alkyl(cycloalkylidene)-carbonyl amino acid derivatives useful as endothelin convening enzyme inhibitors are described.

In the British patent application No. 2116559 (Squibb & Sons, Inc.) some phosphinic acid derivatives with ACE-inhibitory activity are described among which, in particular, the compounds of formula

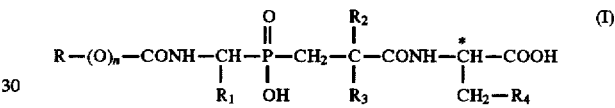

wherein $R_5$ and $R_6$, the same or different, represent a hydrogen atom, an alkyl, phenyl or phenylalkyl group with from 1 to 10 carbon atoms in the alkyl moiety; $R_3$ represents an aminoalkyl or imidazolylalkyl group with from 1 to 5 carbon atoms in the alkyl moiety; $R_{17}$ represents an alkyl, phenylalkyl, imidazolylalkyl or indolylalkyl group with from 1 to 4 carbon atoms in the alkyl moiety; n is 0 or 1.

In the work published by D. Grobelny et al. in Biochemistry 1989, 28, 4948–4951, some phosphinic acid derivatives are described among which, in particular, the compound N-[3-[(benzyloxycarbonylaminomethyl)(hydroxy)phosphinyl]-2-isobutyl-propionyl]-leucine as inhibitor of thermolysin, an endopeptidase of bacterial origin.

Subsequently, as reported by Brandley P. Morgan et al. in Pept. Chem. Struct. Biol., Proc. Am. Pept. Symp., 11th, 1989, 371–2 (Chemical Abstracts 115:44857, 1991) and in Journal of the American Chemical Society 1991, 113, 297–307, and by G. Klebe et al. in Journal of Medicinal Chemistry 1993, 36, 70–80, some phosphinic acid derivatives are described among which, in particular, the compounds of formula

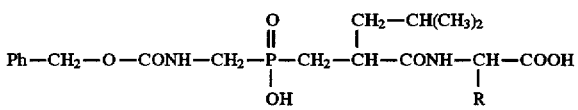

wherein Ph is a phenyl group and R represents a hydrogen atom or a methyl, isobutyl or benzyl group, and corresponding lithium salts thereof, endowed with inhibitory activity towards thermolysin.

In the International patent application No. WO 95/35302 in the name of the instant Applicant some phosphinic acid derivatives are described among which, in particular, the derivatives of N-(phosphinyl-alkanoyl)-biphenylalanine, endowed with ACE-inhibitory and NEP-inhibitory activity.

Now we have found phosphinic acid derivatives which are endowed with an inhibitory activity on the angiotensin converting enzyme as well as on the neutral endopeptidase enzyme (dual ACE/NEP-inhibitory activity) which makes them particularly useful in the cardiovascular therapy.

Therefore, object of the present invention are the compounds of formula

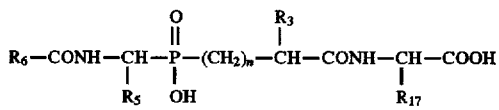

wherein

R is a straight or branched $C_1$–$C_4$ alkyl group, a 5 or 6 membered aromatic heterocyclic group with 1 or 2 heteroatoms selected among nitrogen, oxygen and sulphur optionally substituted with a $C_1$–$C_3$ alkyl group or a phenyl or phenylalkyl group with from 1 to 4 carbon atoms in the alkyl moiety, optionally substituted with one or more substituents, the same or different, selected among hydroxy groups, alkoxy, alkylthio, alkylsulphonyl or alkoxycarbonyl groups with from 1 to 3 carbon atoms in the alkyl moiety, carboxy groups, aminocarbonyl groups, acylamino groups, aminosulphonyl groups, mono- or di-alkylaminocarbonyl groups with from 1 to 3 carbon atoms in the alkyl moiety;

$R_1$ is a hydrogen atom or a straight or branched $C_1$–$C_4$ alkyl group;

$R_2$ is a straight or branched $C_3$–$C_6$ alkyl group, a 2-methoxy-ethoxymethyl group or an arylmethyl group wherein the aryl is a phenyl group or a 5 or 6 membered aromatic heterocyclic group with one or two heteroatoms selected among nitrogen, oxygen and sulphur, the phenyl group being optionally substituted with a methylenedioxy group or with one or more substituents, the same or different, selected among halogen atoms, hydroxy groups, alkoxy, alkylthio, alkylsulphonyl or alkoxycarbonyl groups with from 1 to 3 carbon atoms in the alkyl moiety, aminocarbonyl groups, acylamino groups, aminosulphonyl groups, mono- or di-alkylaminocarbonyl groups with from 1 to 3 carbon atoms in the alkyl moiety;

$R_3$ is a hydrogen atom;

$R_4$ is a 5 or 6 membered aromatic heterocyclic group with one or two heteroatoms selected among nitrogen, oxygen and sulphur, a phenyl group optionally substituted with an aryl group wherein the aryl is a phenyl or a 5 or 6 membered aromatic heterocycle cycle with one or two heteroatoms selected among nitrogen, oxygen and sulphur or a phenyl group optionally substituted with one or more substituents, the same or different, selected among halogen atoms, hydroxy groups, alkoxy, alkylthio or alkoxycarbonyl groups with from 1 to 3 carbon atoms in the alkyl moiety, carboxy groups, aminocarbonyl groups, acylamino groups, aminosulphonyl groups, mono- or di-alkylaminocarbonyl groups with from 1 to 3 carbon atoms in the alkyl moiety;

n is 0 or 1;

the carbon atom marked with an asterisk is a stereogenic center;

and pharmaceutically acceptable salts thereof;

provided that a) when $R_1$ is equal to hydrogen and $R_4$ is equal to biphenyl, n is 1;

b) when $R_4$ is equal to phenyl or imidazolyl and $R_2$ is equal to imidazolylmethyl, n is 1;

the compound N-[3-[(benzyloxycarbonylaminomethyl (hydroxy)phosphinyl]-2-isobutyl-propionyl]-phenylalanine and its lithium salt being excluded.

The compounds of formula I contain at least a stereogenic center and can thus exist in the form of stereoisomers.

Therefore, object of the present invention are the compounds of formula I in the form of stereoisomeric mixtures as well as in the form of single stereoisomers.

The compounds of formula I object of the present invention are endowed with a dual ACE-inhibitory and NEP-inhibitory activity and are useful in the treatment of cardiovascular diseases.

In the present description, unless otherwise specified, with the term alkyl group we intend a straight or branched alkyl such as methyl, ethyl, n.propyl, isopropyl, n.butyl, sec-butyl, tert-butyl, isobutyl, n.pentyl, 2-pentyl, 3-pentyl, isopentyl, tert-pentyl, n.hexyl and isohexyl; with the term alkoxy group we intend a straight or branched alkoxy such as methoxy, ethoxy, n.propoxy and isopropoxy; with the term halogen atom we intend a fluorine, chlorine, bromine or iodine atom; with the term acyl we intend an acyl group deriving from an aliphatic or aromatic carboxylic acid such as acetic, propionic, butyric and benzoic acid; with the term aryl we intend an aromatic group such as phenyl or a 5 or 6 membered heterocyclic group containing 1 or 2 heteroatoms selected among nitrogen, oxygen and sulphur such as thiazole, isoxazole, oxazole, isothiazole, pyrazole, imidazole, thiophene, pyrrole, pyridine, pyrimidine and Examples of pharmaceutically acceptable salts of the compounds of formula I are the salts with alkali or alkaline-earth metals and the salts with pharmaceutically acceptable organic bases.

Preferred compounds of formula I are the compounds wherein R is a straight or branched $C_1$–$C_4$ alkyl group or a group selected among phenyl, benzyl, pyridyl or isoxazolyl; $R_1$ is a hydrogen atom; $R_2$ is a branched $C_3$–$C_4$ alkyl group or an arylmethyl group wherein the aryl is phenyl, pyridyl or thienyl; $R_3$ is a hydrogen atom and $R_4$ is a phenyl group optionally substituted by an aryl group wherein the aryl is selected among phenyl, pyridyl or thiazolyl.

Still more preferred compounds of formula I are the compounds wherein R is a straight or branched $C_1$–$C_4$ alkyl group or a group selected among phenyl, benzyl, pyridyl or isoxazolyl; $R_1$ is a hydrogen atom; $R_2$ is a branched $C_3$–$C_4$ alkyl group or an arylmethyl group wherein the aryl is phenyl, pyridyl or thienyl; $R_3$ is a hydrogen atom; $R_4$ is a phenyl group optionally substituted by an aryl group wherein the aryl is selected among phenyl, pyridyl or thiazolyl and n=1.

Preferred examples of pharmaceutically acceptable salts of the compounds of formula I are the salts with alkali metals such as sodium, lithium and potassium.

Specific examples of the compounds of formula I, object of the present invention, are:

N-[3-[(1-benzyloxycarbonylamino-ethyl)(hydroxy) phosphinyl]-2-isobutyl-propionyl]-(1,1'-biphenyl-4-yl)-L-alanine;

N-[3-[(benzyloxycarbonylaminomethyl)(hydroxy) phosphinyl]-2-isobutyl-propionyl]-(1,1'-biphenyl-4-yl)-L-alanine;

N-[3-[(ethoxycarbonylaminomethyl)(hydroxy) phosphinyl]-2-isobutyl-propionyl]-(1,1'-biphenyl-4-yl)-L-alanine;

N-[3-[(tert-butoxycarbonylaminomethyl)(hydroxy) phosphinyl]-2-isobutyl-propionyl]-(1,1'-biphenyl-4-yl)-L-alanine;

N-[3-[(benzyloxycarbonylaminomethyl)(hydroxy) phosphinyl]-2-isopropyl-propionyl]-(1,1'-biphenyl-4-yl)-L-alanine;

N-[3-[(benzyloxycarbonylaminomethyl)(hydroxy) phosphinyl]-2-benzyl-propionyl]-(1,1'-biphenyl-4-yl)-L-alanine;

N-[3-[(benzyloxycarbonylaminomethyl)(hydroxy) phosphinyl]-2-(4-chlorobenzyl)-propionyl]-(1,1'-biphenyl-4-yl)-L-alanine;

N-[3-[(benzyloxycarbonylaminomethyl)(hydroxy) phosphinyl]-2-(2-thienylmethyl)-propionyl]-(1,1'-biphenyl-4-yl)-L-alanine;

N-[3-[(benzyloxycarbonylaminomethyl)(hydroxy) phosphinyl]-2-(3-pyridylmethyl)-propionyl]-(1,1'-biphenyl-4-yl)-L-alanine;

N-[3-[(benzyloxycarbonylaminomethyl(hydroxy) phosphinyl]-2-(3,4-methylenedioxy-phenyl-methyl)-propionyl]-(1,1'-biphenyl-4-yl)-L-alanine;

N-[3-[(benzyloxycarbonylaminomethyl(hydroxy) phosphinyl]-2-isobutyl-propionyl]-L-tyrosine;

N-[3-[(benzyloxycarbonylaminomethyl(hydroxy) phosphinyl]-2-isobutyl-propionyl]-(4-fluorophenyl)-L-alanine;

N-[3-[(benzyloxycarbonylaminomethyl)(hydroxy) phosphinyl]-2-isobutyl-propionyl]-(3-pyridyl)-L-alanine;

N-[3-[(benzyloxycarbonylaminomethyl)(hydroxy) phosphinyl]-2-isobutyl-propionyl]-(3-thienyl)-L-alanine;

N-[3-[(benzyloxycarbonylaminomethyl)(hydroxy) phosphinyl]-2-isobutyl-propionyl]-[4-(2-furyl)-phenyl]-L-alanine;

N-[3-[(benzyloxycarbonylaminomethyl(hydroxy) phosphinyl]-2-isobutyl-propionyl]-[4-(3-pyridyl)-phenyl]-L-alanine;

N-[3-[(benzyloxycarbonylaminomethyl)(hydroxy) phosphinyl]-2-isobutyl-propionyl]-[4-(5-pirimidinyl)-phenyl]-L-alanine;

N-[3-[(benzyloxycarbonylaminomethyl)(hydroxy) phosphinyl]-2-isobutyl-propionyl]-[4-(2-thiazolyl)-phenyl]-L-alanine;

N-[3-[(benzoylaminomethyl)(hydroxy)phosphinyl]-2-isobutyl-propionyl]-L-phenyl-alanine;

N-[3-[(benzoylaminomethyl)(hydroxy)phosphinyl]-2-isobutyl-propionyl]-L-tirosine;

N-[3-[(benzoylaminomethyl)(hydroxy)phosphinyl]-2-isobutyl-propionyl]-(4-fluoro-phenyl)-L-alanine;

N-[3-[(benzoylaminomethyl)(hydroxy)phosphinyl]-2-isobutyl-propionyl]-(3-pyridyl)-L-alanine;

N-[3-[(benzoylaminomethyl)(hydroxy)phosphinyl]-2-isobutyl-propionyl]-(3-thienyl)-L-alanine;

N-[3-[(benzoylaminomethyl)(hydroxy)phosphinyl]-2-isobutyl-propionyl]-[4-(2-furyl)-phenyl]-L-alanine;

N-[3-[(benzoylaminomethyl(hydroxy)phosphinyl]-2-isobutyl-propionyl]- [4-(3-pyridyl)-phenyl]-L-alanine;

N-[3-[(benzoylaminomethyl(hydroxy)phosphinyl]-2-isobutyl-propionyl]-[4-(5-pirimidinyl)-phenyl]-L-alanine;

N-[3-[(benzoylaminomethyl(hydroxy)phosphinyl]-2-isobutyl-propionyl]-[4-(2-thiazolyl)-phenyl]-L-alanine;

N-[3-[(3-methyl-5-isoxazolyl-carbonylaminomethyl (hydroxy)phosphinyl]-2-isobutyl-propionyl]-L-phenylalanine;

N-[3-[(2-furyl-carbonylaminomethyl)(hydroxy) phosphinyl]-2-isobutyl-propionyl]-L-phenylalanine;

N-[3-[(3-pyridyl-carbonylaminomethyl)(hydroxy) phosphinyl]-2-isobutyl-propionyl]-L-phenylalanine.

The preparation of the compounds of formula I, object of the present invention, comprises the reaction between a compound of formula

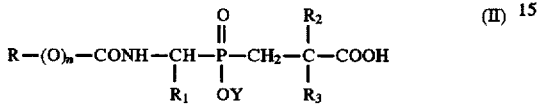

wherein

R, R$_1$, R$_2$, R$_3$ and n have the above reported meanings and Y represents a protective group, preferably a C$_1$–C$_4$ alkyl, a phenyl or a phenylalkyl having from 1 to 4 carbon atoms in the alkyl moiety;

and an alanine derivative of formula

wherein

R$_4$ has the above reported meanings.

The condensation reaction is carried out according to conventional techniques of the chemistry of peptides.

Before carrying out the reaction, it can be useful to properly protect the optional functional groups which could interfere in the reaction.

The optional protection is carried out according to conventional techniques.

For instance besides the OH function of the phosphinic group it can be useful to protect the free carboxy function of the compound of formula III.

The evaluation of the usefulness of the optional protection as well as the selection of the kind of adopted protection, according to the reaction to be carried out and to the functional groups to be protected, are within the normal knowledge of the man skilled in the art.

The removal of the optional protective groups is carried out according to conventional techniques.

For a general reference to the use of protective groups in organic chemistry see Theodora W. Greene and Peter G. M. Wuts "Protective Groups in Organic Synthesis", John Wiley & Sons, Inc., II Ed., 1991.

The compounds of formula II and III are known or easily prepared according to known methods.

For instance, the compounds of formula II wherein n=1 can be prepared as described in J. Med. Chem 1988, 31, 1772-1778.

The compounds of formula II wherein n=0, instead, can be prepared from the corresponding compounds of formula II wherein n=1 and R=benzyl by hydrogenolysis of the carbamic group (R—O—CONH—), carried out according to conventional techniques, and by subsequent reaction with a compound of formula

wherein

R has the above reported meanings and Z represents a chlorine or bromine atom.

The compounds of formula III, instead, can be prepared according to the synthetic methods described by W. C. Shieh et al. in J. Org. Chem. 1992, 57, 379–381.

Alternatively, the compounds of formula III can be prepared by cross-coupling methods starting from halogenated heterocyclic compounds and stannyl phenylalanine derivatives, as described by D. S. Wilbur et al. in Bioconjugate Chem. 1993, 4, 574–580. Moreover, the compounds of formula I, object of the present invention, can be prepared according to an alternative process comprising the reaction between a phosphorylated derivative of formula

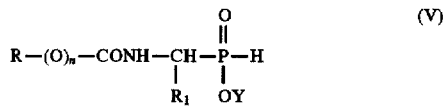

wherein

R, R$_1$, n and Y have the above reported meanings; and a compound of formula

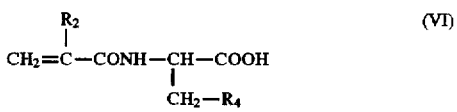

wherein

R$_2$ and R$_4$ have the above reported meanings.

Also the compounds of formula V and VI are known or easily prepared according to known methods.

For instance, the compounds of formula VI can be prepared by reaction between a compound of formula

wherein

R$_2$ has the above reported meanings; and an alanine derivative of formula (III).

Analogously to what previously reported, also in the aforementioned reaction it can be useful to protect, according to conventional techniques, optional functional groups which could interfer in the reaction.

The compounds of formula V wherein n=1 can be prepared, for instance, as described in Bioorg. Med. Chem. Lett., 4, (1994), 1221-1224 and in J. Am. Chem Soc. 1991, 113,297-307.

The compounds of formula V wherein n=0, instead, can be prepared starting from the corresponding compounds of formula V wherein n=1 and R=benzyl, by hydrogenolysis of the carbamic group (R—O—CONH—) and by subsequent reaction with a compound of formula IV.

In view of what above reported it is clear to the man skilled in the an that the preparation of the compounds of formula I wherein n=0 can be optionally carried out starting from the corresponding compounds of formula I wherein n=1 and R=benzyl, prepared according to one of the aforementioned synthetic schemes, by hydrogenolysis of the carbamic group (R—O—CONH) and by subsequent reaction with a compound of formula IV.

The compounds of formula I in the form of single stereoisomers are prepared by stereoselective synthesis or by separation of the stereoisomeric mixture according to conventional techniques.

Also the preparation of the salts of the compounds of formula I, object of the invention, is carried out according to conventional techniques.

The compounds of formula I object of the present invention are endowed with a dual ACE-inhibitory and NEP-inhibitory activity and are useful in the treatment of cardiovascular diseases.

The inhibitory activity of the compounds of formula I was evaluated by means of in vitro tests, in comparison to known molecules endowed with ACE-inhibitory or NEP-inhibitory activity (example 11).

Captopril, a drug known as the first orally active ACE-inhibitor (The Merck Index, XI ed.—No. 1773, pages 267–268), was used as a comparison compound for the ACE-inhibitory activity.

3-[1-[(Cis-4-carboxycyclohexyl)carbamoyl]cyclopentyl]-2-(2-methoxyethoxymethyl)-propionic acid, a compound having NEP-inhibitory activity known as Candoxatrilat and described by K. James et at. in Perspectives in medicinal chemistry, Ed. Bernard Testa et al. (1993), pages 45–60, was used as a comparison compound for the NEP-inhibitory activity.

The inhibitory activity of the compounds of formula I, expressed as $IC_{50}$ value, is pharmacologically significant in that it results at nM concentrations.

Moreover, the inhibitory activity of the compounds of formula I resulted to be comparable to the ACE-inhibitory activity of Captopril and to the NEP-inhibitory activity of Candoxatrilat, respectively.

For a practical use in therapy, the compounds of formula I can be formulated in solid or liquid pharmaceutical compositions, suitable to oral or parenteral administration. Therefore, the pharmaceutical compositions containing a therapeutically effective amount of a compound of formula I in admixture with a carrier for pharmaceutical use are a further object of the present invention.

Specific examples of pharmaceutical compositions according to the present invention are tablets, coated tablets, capsules, granulates, solutions and suspensions suitable to oral administration, solutions and suspensions suitable to parenteral administration. The pharmaceutical compositions object of the present invention are prepared according to conventional techniques.

Although the compounds of formula I are active as such, with the aim to satisfy particular therapeutic or pharmaceutical requirements, it can be useful to transform them into the corresponding biologic precursors (pro-drugs).

Therefore, according to the conventional techniques for the preparation of pro-drugs of phosphorylated or carboxylated derivatives, suitable pro-drugs can be obtained for instance through the esterification of the carboxy function or of the phosphinic function.

Also the compounds of formula I in the form of pro-drugs and, in particular, the compounds obtained through the esterification of the carboxy or phosphinic function as well as the pharmaceutical compositions, which contain the compounds of formula I in the form of pro-drugs and, in particular, which contain the compounds of formula I wherein the carboxy or phosphinic group results to be esterified, are within the scope of the present invention.

The daily dose of the compound of formula I or of the corresponding pro-drug will depend on several factors such as the seriousness of the disease, the individual response of the patient or the kind of formulation but it is usually comprised between 0.01 mg and 20 mg per kg of body weight divided into a single dose or into more daily doses.

With the aim of illustrating the present invention the following examples are now

EXAMPLE 1

Preparation of N-tert-butoxycarbonyl-[4-(2-thiazolyl)-phenyl]-L-alanine methyl ester N-tert-butoxycarbonyl-4-(trifluoromethylsulphonyl)-L-phenylalanine methyl ester (8 g; 32.3 mmoles) and palladium-bis(triphenylphosphine) chloride (2.3 g) were added to a solution of 2-trimethylstannyl-thiazole (13.8 g; 32.3 mmoles) in a mixture of tetrahydrofuran:toluene=10:1 (50 ml), previously degassed with nitrogen.

The mixture was refluxed for 24 hours and, subsequently, 2-trimethylstannyl-thiazole (2 g) was therein added.

After 6 hours under reflux N-tert-butoxycarbonyl-4-(trifluoromethylsulphonyl)-L-phenylalanine methyl ester (2 g) and palladium-bis(triphenylphosphine) chloride (700 mg) were added again.

The resultant reaction mixture was kept under stirring at 70° C. for 16 hours and was subsequently cooled at room temperature.

Water (200 ml) was then added to the mixture which was extracted with methylene chloride (4×200 ml).

The collected organic phases were dried on sodium sulphate and evaporated under vacuum.

The obtained residue was purified by flash chromatography (silica gel, eluent methylene chloride:ethyl acetate=9:1, pressure of nitrogen=0.1 atm, $10^4$ Pa) thus affording N-tert-butoxycarbonyl-[4-(2-thiazolyl)-phenyl]-L-alanine methyl ester (2.3 g; 20% yield).

$^1$H-NMR (200 MHz, $CDCl_3$): δ (ppm): 1.40 [s, 9H, $C(CH_3)_3$]; 3.00–3.21 (m, 2H $CH_2$); 3.70 (s, 3H, $COOCH_3$); 4.42–4.65 (m, 1H, CH—COO); 5.02 (bd, 1H, NH); 7.30 (d, 1H, S—CH—CH—N); 7.81 (d, 1H, S—CH—CH—N); 7.15–7.90 (m, 4H, phenylene).

EXAMPLE 2

Preparation of (1,1'-biphenyl-4-yl)-L-alanine methyl ester hydrochloride

Thionyl chloride (0.043 ml; 0.586 mmoles) was added at room temperature to a solution of N-tert-butoxycarbonyl-(1,1'-biphenyl-4-yl)-L-alanine (100 mg; 0.293 mmoles) in methanol (2 ml).

After 24 hours, the reaction mixture was concentrated at small volume by evaporation under vacuum affording (1,1'-biphenyl-4-yl)-L-alanine methyl ester hydrochloride with a practically quantitative yield (85 mg) as a crystalline solid. m.p. 215°–6° C.

$^1$H-NMR (200 MHz, DMSO-$d_6$): δ (ppm): 3.15 (dd, 2H); 3.70 (s, 3H); 4.30 (t, 1H); 7.25–7.52 (m, 5H); 7.65 (m, 4H).

By working in an analogous way and by using N-tert-butoxycarbonyl-[4-(2-thiazolyl)-phenyl]-L-alanine methyl ester prepared as described in example 1, as starting material, the following compound was prepared:

[4-(2-thiazolyl)-phenyl]-L-alanine methyl ester dihydrochloride $^1$H-NMR (200 MHz, $D_2O$): δ (ppm): 3.10–3.32 (m, 2H, $CH_2$—CH); 3.68 (s, 3H, $CH_3$); 4.30–4.38 (m, 1H, CH); 7.30–7.80 (m, 4H, phenylene); 7.70–7.91 (m, 2H, thiazolyl).

EXAMPLE 3

Preparation of 2-chloromethyl-thiophene

Thionyl chloride (67.35 ml; 0.93 moles) was added dropwise to a cooled solution of 2-hydroxymethyl-thiophene (60.35 g; 0.35 moles) in toluene (400 ml), kept at 0° C. At the end of the addition, the reaction mixture was kept under stirring at room temperature for 48 hours.

The solvent was then evaporated under vacuum and the resultant oil was distilled at 44°–45° C. (4 mmHg, 533 Pa) affording 2-chloromethyl-thiophene (48.9 g; 69% yield) as an oil.

$^1$H-NMR (200 MHz, CDCl$_3$): δ (ppm): 4.80 (s, 2H); 6.95 (dd, 1H); 7.06 (d, 1H); 7.30 (d, 1H).

EXAMPLE 4

Preparation of diethyl 2-thienylmethyl-malonate

A solution of diethyl malonate (129.2 ml; 0.85 moles) in tetrahydrofuran (150 ml) was gradually added to a suspension of sodium hydride (25.5 g; 0.85 moles) in tetrahydrofuran (200 ml), keeping the mixture under stirring for 75 minutes.

A solution of 2-chloromethyl-thiophene (53 g; 0.40 moles) in tetrahydrofuran (130 ml), prepared as described in example 3, was then gradually added to the reaction mixture which was kept under stirring for 16 hours at 40° C.

Subsequently, the mixture was poured into a solution of phosphate buffer pH 7 (3.5 l) and the organic phase was separated.

The aqueous phase was extracted with ethyl ether and the collected organic phases were evaporated under vacuum affording an oil which, distilled in Vigreaux at 100°–104° C. (0.11 mmHg, 15 Pa), furnished diethyl 2-thienylmethyl-malonate (31.49 g; 30.7% yield) as a colourless oil.

$^1$H-NMR (200 MHz, CDCl$_3$): δ (ppm): 1.22 (t, 6H); 3.40 (d, 2H); 3.65 (t, 1H); 4.27 (q, 4H); 6.85 (m, 2H); 7.12 (d, 1H).

EXAMPLE 5

Preparation of 2-thienylmethyl-malonic acid

A solution of diethyl 2-thienylmethyl-malonate (31 g; 121 mmoles) in dioxane, prepared as described in example 4, was added to a solution of potassium hydroxide at 85% (17.55 g; 266 mmoles) in water (53 ml).

The reaction mixture was kept under stirring overnight.

Dioxane was evaporated and the mixture was collected with water (100 ml) and washed with ethyl acetate (50 ml).

The reaction mixture was then acidified with concentrated hydrochloric acid and extracted with ethyl acetate (2×50 ml).

The separated organic phase was dried on sodium sulphate and evaporated to dryness affording 2-thienylmethyl-malonic acid (23.45 g; 97% yield) as a white solid.

$^1$H-NMR (200 MHz, DMSO-d$_6$): δ (ppm): 3.21 (d, 2H); 3.55 (t, 1H); 6.90 (m, 2H); 7.31 (d, 1H).

EXAMPLE 6

Preparation of 2-(2-thienylmethyl)-acrylic acid

An aqueous solution of dimethylamine at 40% (25.31 ml; 0.20 moles) and an aqueous solution of formaldehyde at 37% (15 ml; 0.20 moles) were respectively added, at 0° C., to a solution of 2-thienylmethyl-malonic acid (35.16 g; 0.18 moles) in water (56 ml), prepared as described in example 5.

The reaction mixture was kept under stirring for 3 hours at 0° C. and subsequently, at room temperature, it was diluted with water (50 ml) and extracted with ethyl acetate (2×100 ml).

The separated organic phase was dried on sodium sulphate and evaporated to dryness. The resultant oil was heated under vacuum at 50° C. (12 mmHg, 1600 Pa) for 12 hours and the resultant crude product was purified by silica gel column chromatography (eluent methylene chloride:methanol=95:5) affording 2-(2-thienylmethyl)-acrylic acid (15.1 g; 50% yield).

$^1$H-NMR (200 MHz, CDCl$_3$): δ (ppm): 3.81 (s, 2H); 5.70 (s, 1H); 6.40 (s, 1H); 6.85 (d, 1H); 6.94 (dd, 1H); 7.15 (d, 1H).

EXAMPLE 7

Preparation of N-(2-isobutyl-acryloyl)-(1,1'-biphenyl-4-yl)-L-alanine methyl ester A suspension of (1,1'-biphenyl-4-yl)-L-alanine methyl ester hydrochloride (7.03 g; 24 mmoles), prepared as described in example 2, 2-isobutyl-acrylic acid (3.7 g; 28.9 mmoles), triethylamine (4.01 ml; 28.9 mmoles) and dicyclohexylcarbodiimide (5.95 g; 28.9 mmoles) in methylene chloride (140 ml) was kept under stirring at room temperature for 21 hours.

Subsequently, the obtained precipitate was filtered off and the organic phase was washed with water, dried on sodium sulphate and evaporated under reduced pressure. The resultant oil was purified by silica gel chromatography (eluent petroleum ether 40°–60° C.:ethyl acetate=80:20) thus affording N-(2-isobutyl-acryloyl)-(1,1'-biphenyl-4-yl)-alanine methyl ester (4.17 g; 47% yield) as a white solid.

$^1$H-NMR (200 MHz, CDCl$_3$): δ (ppm): 0.93 (d, 6H); 1.50–1.75 (m, 1H); 2.15 (d, 2H); 3.08–3.30 (m, 2H); 3.75 (s, 3H); 4.95 (m, 1H); 5.21 (s, 1H); 5.58 (s, 1H); 7.60 (m, 9H).

By working in an analogous way and by using 2-benzyl-acrylic acid or 2-(2-thienyl-methyl)-acrylic acid in place of 2-isobutyl-acrylic acid, as starting materials, the following compounds were prepared:

N-(2-benzyl-acryloyl)-(1,1'-biphenyl-4-yl)-L-alanine ethyl ester $^1$H-NMR (200 MHz, CDCl$_3$): δ (ppm): 1.22 (t, 3H); 3.12 (d, 2H); 3.63 (dd, 2H); 4.15 (q, 2H); 4.86 (q, 1H); 5.27 (s, 1H); 5.72 (s, 1H); 6.21 (bd, 1H); 6.90–7.60 (m, 14H);

N-[2-(2-thienylmethyl)-acryloyl]-(1,1'-biphenyl-4-yl)-L-alanine methyl ester $^1$H-NMR (200 MHz, CDCl$_3$): δ (ppm): 3.15 (t, 2H); 3.72 (s, 3H); 3.83 (d, 2H); 4.92 (m, 1H); 5.40 (s, 1H); 5.71 (s, 1H); 6.28 (bd, 1H); 6.80 (d, 1H); 6.90 (m, 1H); 7.05 (d, 2H); 7.14 (d, 1H); 7.30–7.60 (m, 7H).

EXAMPLE 8

Preparation of N-[3-[(1-benzyloxycarbonylamino-ethyl)(methoxy)phosphinyl]-2-isobutyl-propionyl]-(1,1'-biphenyl-4-yl)-L-alanine methyl ester A solution of sodium methylate obtained by dissolving metallic sodium (0.132 g; 5.7 mmoles) in methanol (6 ml) was gradually added, under nitrogen atmosphere at 0° C., to a solution of methyl (1-benzyloxycarbonylamino-ethyl) phosphinate (1.48 g; 5.75 mmoles) and N-(2-isobutyl-acryloyl)-(1,1'-biphenyl-4-yl)-L,-alanine methyl ester (2.1 g; 5.75 mmoles), prepared as described in example 7, in methanol (6 ml).

The reaction mixture was kept under stirring at 50° C. for 21 hours and, cooled at room temperature, was then added to an aqueous solution of diluted hydrochloric acid and extracted with ethyl acetate.

The organic phase, washed with water, with a saturated aqueous solution of sodium bicarbonate and with water again, was dried on sodium sulphate and evaporated under reduced pressure.

The residue (3.9 g) was purified by silica gel chromatography (eluent methylene chloride:methanol=97:3) affording N-[3-[(1-benzyloxycarbonylamino-ethyl(methoxy)-phosphinyl]-2-isobutyl-propionyl]-(1,1'-biphenyl-4-yl)-L-alanine methyl ester (2.2 g; 61% yield) as an oil.

$^1$H-NMR (200 MHz, CDCl$_3$): δ (ppm): 0.65–0.95 (m, 6H); 1.10–2.30 (m, 8H); 2.60 (m, 1H); 2.95–3.25 (m, 2H); 3.50–3.80 (m, 6H); 4.05 (m, 1H); 4.80–5.20 (m, 3H); 7.10–7.60 (m, 14H).

By working in an analogous way and by using the alanine derivatives prepared as described in example 7, as starting materials, the following compounds were prepared:

N-[3-[(benzyloxycarbonylaminomethyl)(methoxy) phosphinyl]-2-benzyl-propionyl]-(1,1'-biphenyl-4-yl)-L-alanine ethyl ester $^1$H-NMR (200 MHz, CDCl$_3$): δ (ppm): 1.18 (m, 3H); 1.60–2.00 (m, 2H); 2.10–2.40 (m, 1H); 2.70–3.15 (m, 4H); 3.30–3.80 (m, 5H); 3.90–4.20 (m, 2H); 4.65–4.90 (m, 1H); 5.00–5.10 (m, 2H); 6.55 (bt, 1H); 6.83 (m, 1H); 7.05–7.60 (m, 19H);

N-[3-[(benzyloxycarbonylaminomethyl)methoxy) phosphinyl]-2-(2-thienylmethyl)propionyl]-(1,1'-biphenyl-4-yl)-L-alanine methyl ester $^1$H-NMR (200 MHz, CDCl$_3$): δ (ppm): 1.65–2.05 (m, 1H); 2.20–2.40 (m, 1H); 2.80–3.70 (m, 13H); 4.80 (m, 1H); 5.06 (s, 2H); 6.75 (d, 1H); 6.87 (t, 1H); 7.05–7.60 (m, 15H).

EXAMPLE 9

Preparation of N-[3-[(benzyloxycarbonylaminomethyl) (methoxy)phosphinyl]-2-isobutyl-propionyl]-(1,1'-biphenyl-4-yl)-L-alanine methyl ester A mixture of 3-[(benzyloxycarbonylaminomethyl) (methoxy)phosphinyl]-2-isobutylpropionic acid (0.35 g; 0.94 mmoles), N-hydroxysuccinimide (0.108 g; 0.94 mmoles) and dicyclohexylcarbodiimide (0.213 g; 1.03 mmoles) in dioxane (10 ml) was kept under stirring at room temperature for 2 hours.

The resultant precipitate was filtered off and (1,1'-biphenyl-4-yl)-L-alanine methyl ester hydrochloride (0.249 g; 0.856 mmoles), prepared as described in example 2, and triethylamine (0. 143 ml; 1.03 mmoles) were added to the resultant solution.

The reaction mixture was heated at 60° C. for 4 hours and, subsequently, was cooled and diluted with ethyl acetate.

The mixture was then treated with an aqueous solution of 5% potassium bisulphate and water.

The separated organic phase was dried on sodium sulphate and evaporated under reduced pressure.

The reaction crude was purified by silica gel chromatography (eluent methylene chloride:methanol 95:5) thus affording N-[3-[(benzyloxycarbonylaminomethyl)- (methoxy)phosphinyl]-2-isobutyl-propionyl]-(1,1'-biphenyl-4-yl)-L-alanine methyl ester (0.45 g; 86% yield) as an amorphous solid.

$^1$H-NMR (200 MHz, CDCl$_3$): δ (ppm): 0.80–0.90 (m, 6H); 1.00–2.30 (m, 5H); 2.50–2.80 (m, 1H); 3.12 (bd, 2H); 3.30–3.80 (m, 8H); 4.86 (m, 1H); 5.07 (dd, 2H); 7.18–7.58 (m, 14H).

By working in an analogous way and by using [4-(2-thiazolyl)-phenyl]-L-alanine methyl ester dihydrochloride prepared as described in example 2, as starting material, the following compound which was used as such in the subsequent reaction without further purification was prepared:

N-[3-[(benzyloxycarbonylaminomethyl)(methoxy) phosphinyl]-2-isobutyl-propionyl]-[4-(2-thiazolyl)-phenyl]-L-alanine methyl ester.

EXAMPLE 10

Preparation of N-[3-(1-benzyloxycarbonylamino-ethyl) (hydroxy)phosphinyl]-2-isobutyl-propionyl]-(1,1'-biphenyl-4-yl)-L-alanine (Compound 1)

A mixture of lithium hydroxide monohydrate (0.519 g; 13.8 mmoles) and N-[3-[(1-benzyloxycarbonylamino-ethyl) (methoxy)phosphinyl]-2-isobutyl-propionyl]-( 1,1'-biphenyl-4-yl)-L-alanine methyl ester (2.15 g; 3.45 mmoles), prepared as described in example 8, in tetrahydrofuran (40 ml) and water (40 ml), was kept under stirring at room temperature under nitrogen atmosphere for 16 hours.

The reaction mixture was then diluted with water, acidified with hydrochloric acid and extracted with ethyl acetate.

The organic phase, washed with water and dried on sodium sulphate, was evaporated under reduced pressure.

The obtained residue was purified by silica gel chromatography (eluent methylene chloride:methanol=94:6) furnishing N-[3-(1-benzyloxycarbonylamino-ethyl)(hydroxy) phosphinyl]-2-isobutyl-propionyl]-(1,1'-biphenyl-4-yl)-L-alanine (0.74 g) as a solid.

$^1$H-NMR (200 MHz, CDCl$_3$+D$_2$O): δ (ppm): 0.68–0.90 (m, 6H); 1.05–2.20 (m, 8H); 2.70 (m, 1H); 3.02–3.30 (m, 2H); 3.95 (m, 1H); 4.61 (m, 1H); 5.03 (m, 2H); 7.18–7.55 (m, 14H).

By working in an analogous way the following compounds were prepared:

N-[3-[(benzyloxycarbonylaminomethyl)(hydroxy) phosphinyl]-2-isobutyl-propionyl]-(1,1'-biphenyl-4-yl)-L-alanine (Compound 2)

m.p. 195°–196° C.

$^1$H-NMR (200 MHz, DMSO-d$_6$+D$_2$O): δ (ppm): 0.70–0.85 (2d, 6H); 1.15–1.90 (m, 5H); 2.50–2.70 (m, 1H); 2.80–3.40 (m, 4H); 4.45 (dd, 1H); 4.97 (s, 2H); 7.20–7.60 (m, 14H);

N-[3-[(benzyloxycarbonylaminomethyl)(hydroxy) phosphinyl]-2-benzyl-propionyl]-(1,1'-biphenyl-4-yl)-L-alanine (Compound 3)

$^1$H-NMR (200 MHz, DMSO-d$_6$+D$_2$O): δ (ppm): 1.40–1.90 (m, 2H); 2.60–3.30 (m, 7H); 4.40 (q, 1H); 4.96 (s, 2H); 6.90–7.60 (m, 19H);

N-[3-[(benzyloxycarbonylaminomethyl)(hydroxy) phosphinyl]-2-(2-thienylmethyl)propionyl]-(1,1'-biphenyl-4-yl)-L-alanine (Compound 4)

Mass (C.I.): (M+H)$^+$: 621

$^1$H-NMR (200 MHz, D$_2$O+NaHCO$_3$): δ (ppm): 1.30–1.80 (m, 2H); 2.40–3.30 (m, 7H); 4.25 (m, 1H); 4.65 (d, 2H); 6.20–7.45 (m, 17H);

N-[3-[(benzyloxycarbonylaminomethyl)(hydroxy) phosphinyl]-2-isobutyl-propionyl]-[4-(2-thiazolyl)-phenyl]-L-alanine (Compound 5)

Mass (C.I.): (M-H)$^-$: 586

$^1$H-NMR (200 MHz, D$_2$O+NaHCO$_3$): δ (ppm): 0.59 (d, 3H, JHH=5.8 Hz, CH$_3$—CH); 0.64 (d, 3H, JHH=5.7 Hz, CH$_3$—CH); 1.06–1.46 (m, 5H, P—CH$_2$—CH—CH$_2$—CH); 2.34–3.12 (m, 5H, NH—CH$_2$—P—CH$_2$—CH and CONH—CH—CH$_2$); 4.32–4.40 (m, 1H, CH—COO); 4.67–4.81 (m, 2H, CH$_2$-phenyl); 7.04–7.67 (m, 11H, aryl).

EXAMPLE 11

In vitro evaluation of the pharmacologic activity a) NEP-inhibitory activity

The NEP-inhibitory activity was evaluated in rat kidney cortex membranes prepared according to the procedure described by T. Maeda et al. in Biochim biophys. Acta 1983, 731 (1), 115–120.

By working at 0°–4° C. kidneys were removed from male Sprague-Dawley rats weighing approximately 300 g.

Kidney cortex was carefully dissected, finely minced and suspended in a homogenization buffer (10 mM sodium phosphate pH 7.4 containing 1 mM MgCl$_2$, 30 mM NaCl, 0.02% NaN$_3$) 1:15 weight/volume.

The tissue was then homogenized for 30 seconds by using an Ultra-Turrax homogenizer.

Approximately 10 ml of homogenate were layered over 10 ml of sucrose (41% weight/volume) and centrifuged at 31200 rpm for 30 minutes at 4° C. in a fixed angle rotor.

The membranes were collected from the buffer/sucrose interface, washed twice with 50 mM TRIS/HCl buffer (pH 7.4) and resuspended into the same buffer for storage.

The membranes were stored in small aliquots at −80° C. until use.

The NEP-inhibitory activity was evaluated according to the method described by C. Llorens et al., in Eur. I. Pharmacol., 69, (1981), 113–116, as reported hereinafter.

Aliquots of the membrane suspension prepared as above described (concentration 5 μg/ml of proteins) were preincubated in the presence of an aminopeptidase inhibitor (Bestatin—1 mM) for 10 minutes at 30° C.

[$^3$H]|Leu$^5$]-enkephaline (15 nM) and buffer TRIS/HCl pH 7.4 (50 mM) were added in order to obtain a final volume of 100 μl.

Incubation (20 minutes at 30° C.) was stopped by adding HCl 0.1 M (100 μl).

The formation of the metabolite [$^3$H]Tyr-Gly-Gly was quantified, after separation of the unreacted substrate by chromatography on polystirene columns (Porapak Q), by measuring the relative radioactivity through liquid scintillation.

The percentage of inhibition of the metabolite formation in the membrane preparations treated with the compounds of formula I and with the comparative compounds with respect to the untreated membrane preparations was expressed as IC$_{50}$ (nM) value.

b) ACE-inhibitory activity

The ACE-inhibitory activity was evaluated according to the method reported in the literature by B. Holmquist et al., in Analytical Biochemistry 95, 540–548 (1979).

50 μM of ACE (250 mU/ml purified by lung rabbit, EC 3.4.15.1 SIGMA) were preincubated with 50 μl of the compound of formula I or of the comparison compound in thermostated cuvettes at 37° C.

The reaction was started by adding furylacryloylphenylalanylglycylglycine 0.8 mM (FAPGG-SIGMA).

Contemporaneously, by using a Beckman DU-50 spectrophotometer provided with a program for calculating delta A/minutes and regression coefficients of the enzyme kinetics curves, the absorbance at 340 10$^{-9}$ m was recorded in continuo for 5 minutes.

The percentage of enzyme inhibition in the preparations treated with the compounds of formula I or with the comparison compounds with respect to the untreated preparations was expressed as IC$_{50}$ (nM) value.

The compounds of formula I were tested in the form of lithium salts.

The IC$_{50}$ (nM) values related to the ACE-inhibitory and NEP-inhibitory activity of compounds 2–5 and of the comparison compounds Candoxatrilat and Captopril are reported in the following table 1.

TABLE 1

| Compound | ACE-inhibitory activity IC$_{50}$ (nM) | NEP-inhibitory activity IC$_{50}$ (nM) |
|---|---|---|
| 2 | 6.4 | 36 |
| 3 | 30 | 252 |
| 4 | 12 | 335 |
| 5 | 25 | 48.5 |
| Candoxatrilat | not active | 160 |
| Captopril | 2.8 | not active |

ACE-inhibitory and NEP-inhibitory activity, expressed as IC$_{50}$ (nM), value of compound 2, of compound 3, of compound 4, of compound 5, of Candoxatrilat and of Captopril.

The data reported in table 1 show that the compounds of formula I, object of the present invention, are endowed with a significant dual ACE/NEP-inhibitory activity. Moreover, the inhibitory activity of the compounds of formula I resulted to be comparable to the ACE-inhibitory activity of Captopril as well as to the NEP-inhibitory activity of Candoxatrilat.

What we claim is:

1. A compound of formula

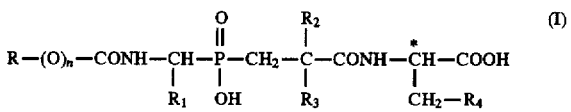

wherein

R is a straight or branched C$_1$–C$_4$ alkyl group, a 5 or 6 membered aromatic heterocyclic group with 1 or 2 heteroatoms selected among nitrogen, oxygen and sulphur optionally substituted with a C$_1$–C$_3$ alkyl group or a phenyl or phenylalkyl group from 1 to 4 carbon atoms in the alkyl group, optionally substituted with one or more substituents, the same or different, selected among hydroxy groups, alkoxy, alkylthio, alkylsulphonyl or alkoxycarbonyl groups with from 1 to 3 carbon atoms in the alkyl group, carboxy groups, aminocarbonyl groups, acylamino groups, aminosulphonyl groups, mono- or di-alkylaminocarbonyl groups with from 1 to 3 carbon atoms in the alkyl group;

R$_1$ is a hydrogen atom or a straight or branched C$_1$–C$_4$ alkyl group;

R$_2$ is a straight or branched C$_3$–C$_6$ alkyl group, a 2-methoxy-ethoxymethyl group or an arylmethyl group wherein the aryl is a phenyl group or a 5 or 6 membered aromatic heterocyclic group with one or two heteroatoms selected among nitrogen, oxygen and sulphur, being the phenyl group optionally substituted with a methylenedioxy group or with one or more substituents, the same or different, selected among halogen atoms, hydroxy groups, alkoxy, alkylthio, alkylsulphonyl or alkoxycarbonyl groups with from 1 to 3 carbon atoms in the alkyl group, aminocarbonyl groups, acylamino groups, aminosulphonyl groups, mono- or di-alkylaminocarbonyl groups with from 1 to 3 carbon atoms in the alkyl group;

R$_3$ is a hydrogen atom or;

R$_4$ is a 5 or 6 membered aromatic heterocyclic group with one or two heteroatoms selected among nitrogen, oxygen and sulphur, a phenyl group optionally substituted with an aryl group wherein the aryl is a phenyl or a 5 or 6 membered aromatic heterocycle with one or two heteroatoms selected among nitrogen, oxygen and sulphur or a phenyl group optionally substituted with one or more substituents, the same or different, selected among halogen atoms, hydroxy groups, alkoxy, alkylthio or alkoxycarbonyl groups with from 1 to 3 carbon atoms in the alkyl group, carboxy groups, aminocarbonyl groups, acylamino groups, aminosulphonyl groups, mono- or di-alkylaminocarbonyl groups with from 1 to 3 carbon atoms in the alkyl group;

n is 0 or 1;

the carbon atom marked with an asterisk is a stereogenic center;

and pharmaceutically acceptable salts thereof;

provided that a) when $R_1$ is equal to hydrogen and $R_4$ is equal to biphenyl, n is 1;

b) when $R_4$ is equal to phenyl or imidazolyl and $R_2$ is equal to imidazolylmethyl, n is 1;

the compound N-[3-[(benzyloxycarbonylaminomethyl)(hydroxy)phosphinyl]-2-isobutyl-propionyl]-phenylalanine and its lithium salt being excluded.

2. A compound according to claim 1 wherein R is a straight or branched $C_1$-$C_4$ alkyl group or a group selected among phenyl, benzyl, pyridyl or isoxazolyl; $R_1$ is a hydrogen atom; $R_2$ is a branched $C_3$-$C_4$ alkyl group or an arylmethyl group wherein the aryl is phenyl, pyridyl or thienyl; $R_3$ is a hydrogen atom and $R_4$ is a phenyl group optionally substituted by an aryl group wherein the aryl is selected among phenyl, pyridyl or thiazolyl.

3. A compound according to claim 2 wherein n=1.

4. A compound according to claim 1 in the form of a salt with an alkali metal selected among sodium, lithium and potassium.

5. A pharmaceutical composition containing a therapeutically effective amount of a compound according to claim 1 in admixture with a carrier for pharmaceutical use.

6. A pharmaceutical composition according to claim 5 for the treatment of cardiovascular diseases.

7. A method for the treatment of cardiovascular diseases comprising the administration of a therapeutically effective amount of a compound of formula I according to claim 1.

8. A compound according to claim 1 selected from the group consisting of

N-[3-[(benzyloxy-carbonylaminomethyl)(hydroxy)phosphinyl]-2-isobutylpropionyl]-(1,1'-biphenyl-4-yl)-L-alanine, N-[3-[(benzyloxycarbonylaminomethyl)(hydroxy)phosphinyl]-2-benzyl-propionyl]-(1,1'-biphenyl-4-yl)-L-alanine, N-[3-[(benzyloxycarbonylaminomethyl)-(hydroxy)phosphinyl]-2-(2-thiazolylmethyl)-propionyl]-(1,1'-biphenyl-4-yl)-L-alanine, N-[3-[(benzyloxycarbonylaminomethyl) (hydroxy)phosphinyl]-2-isobutyl-propionyl]-[4-(2-thiazolyl)-phenyl]-L-alanine and pharmaceutically acceptable salts thereof.

* * * * *